(12) United States Patent
Iwamoto et al.

(10) Patent No.: US 8,246,570 B2
(45) Date of Patent: Aug. 21, 2012

(54) DEVICE FOR CELL TRANSPLANTATION (75) Inventors: Yukihide Iwamoto, Fukuoka (JP);
Koichi Nakayama, Fukuoka (JP);
Hiromasa Miura, Fukuoka (JP);
Kazuhiro Tanaka, Fukuoka (JP);
Shuichi Matsuda, Fukuoka (JP)

(73) Assignees: Japan Medical Materials Corporation, Osaka (JP); Yukihide Iwamoto, Fukuoka (JP); Koichi Nakayama, Fukuoka (JP)

( * ) Notice: Subject to any disclaimer, the term of this patent is extended or adjusted under 35 U.S.C. 154(b) by 27 days.

(21) Appl. No.: 12/809,104

(22) PCT Filed: Dec. 21, 2007

(86) PCT No.: PCT/JP2007/075343
§ 371 (c)(1),
(2), (4) Date: Dec. 8, 2010

(87) PCT Pub. No.: WO2009/081503
PCT Pub. Date: Jul. 2, 2009

(65) Prior Publication Data
US 2011/0106005 A1    May 5, 2011

(51) Int. Cl.
*A61M 5/31* (2006.01)
*A61B 17/08* (2006.01)

(52) U.S. Cl. ......... 604/59; 604/11; 604/522; 606/213; 606/215; 606/139; 606/232

(58) Field of Classification Search ............ 604/1–3, 604/11, 13–16, 891.1, 522, 57, 59–60, 285–286, 604/311; 606/198, 213, 215–216, 228–232
See application file for complete search history.

(56) References Cited

U.S. PATENT DOCUMENTS

| 3,101,713 | A | * | 8/1963 | Sargent | 604/16 |
| 4,276,881 | A | * | 7/1981 | Lilaonitkul | 604/14 |
| 5,080,659 | A | * | 1/1992 | Nakanishi | 604/15 |
| 5,496,348 | A | * | 3/1996 | Bonutti | 606/232 |
| 5,545,178 | A | * | 8/1996 | Kensey et al. | 606/213 |
| 2001/0012965 | A1 | | 8/2001 | Masuda et al. | |
| 2008/0091237 | A1 | * | 4/2008 | Schwartz et al. | 606/232 |

FOREIGN PATENT DOCUMENTS

JP    2002-537896 A    11/2002

(Continued)

OTHER PUBLICATIONS

M. Brittberg, et al., Treatment of Deep Cartilage Defects in the Knee with Autologous Chondrocyte Transplantation, The New England Journal of Medicine, vol. 331, No. 14, Oct. 6, 1994, pp. 889-895.

(Continued)

*Primary Examiner* — Quynh-Nhu H Vu
(74) *Attorney, Agent, or Firm* — McDermott Will & Emery LLP (57) ABSTRACT

The present invention provides a cell transplantation device which is capable of inserting cells for transplantation into a cell-deficient site without application of direct external force to the cells. The present invention discloses a cell transplantation device provided with a plate-type carrier with at least one pass-through hole formed on its side surface, a linear member to be threaded through the pass-through hole, and a pusher member which engages with the linear member that comes out from each exit of the pass-through holes.

10 Claims, 13 Drawing Sheets

FOREIGN PATENT DOCUMENTS

| | | |
|---|---|---|
| JP | 2003-304866 A | 10/2003 |
| JP | 2007-75632 A | 3/2007 |
| WO | 97/31517 A2 | 8/1997 |
| WO | 03/087350 A1 | 10/2003 |
| WO | 2005/011765 A1 | 2/2005 |
| WO | 2005/051242 A1 | 6/2005 |

OTHER PUBLICATIONS

Japanese Patent Application No. 2006-172069: Office Action, dated Apr. 27, 2010.

* cited by examiner

DEVICE FOR CELL TRANSPLANTATION

CROSS REFERENCE TO PRIOR APPLICATIONS

This application is a U.S. National Phase application under 35 U.S.C. §371 of International Application No. PCT/JP2007/075343, filed on Dec. 21, 2007. The International Application was published in Japanese on Jul. 2, 2009 as WO 2009/081503 under PCT Article 21(2). The application is herein incorporated by reference.

TECHNICAL FIELD

The present invention relates to a cell transplantation device, specifically a cell transplantation device for the insertion of cells for transplantation into cell-deficient sites.

BACKGROUND OF THE INVENTION

A technology has been proposed in which cells for transplantation are inserted into a cartilage deficient site in a joint (transplantation site) and the deficient site is restored through regeneration of the transplanted cells (Brittberg M., Treatment of deep cartilage defects in the knee with autologous chondrocyte transplantation. N Engl J Med 1994; 331: 889-95). One example of cells used for such transplantation is myeloid stem cell (mesenchymal stem cell, bone marrow stem cell, bone marrow stromal cell; hereinafter called "MSC").

Here, a specific transplantation method will be explained taking an example of a transplantation using a cell plug for cartilage defect in a joint (WO 2005/11765). First, a hole of a predetermined size is formed in a cartilage-deficient site. Then, an autologous cell plug is inserted into the hole. For this purpose, the hole formed in the cartilage should be almost the same shape and size as the cell plug. When the cell plug is inserted, the plug induces the excretion of regeneration factors from the healthy sites surrounding the deficient site as time passes, causing the restoration of the deficient site.

However, since cell plugs themselves are aggregations of cells, they are very soft, and since tweezers or the like are used when technicians insert them into the holes formed in cartilage, it is very difficult to determine the amount of force needed when gripping cell plugs. Further, due to this reason, sometimes cell plugs cannot be fixed at the optimum depth, and sometimes there are cases in which a gap remains between the cell plugs and healthy cells because tweezers must be withdrawn. In addition, the cell plug sometimes becomes damaged when direct force is exerted on the cell plug to push it into a cell-deficient site.

SUMMARY OF THE INVENTION

It is an object of the present invention to provide a cell transplantation device capable of easily inserting cells for transplantation into cell-deficient sites.

The present invention aims at providing a device for transplanting cell structure (also called "plug") that solves the above problems. In order to achieve this object, the present invention takes a constitution that the device is provided with a plate-type carrier with at least one pass-through hole formed on its side surface, a linear member to be threaded through the pass-through hole, and a pusher member that engages with the linear member which comes out from each exit of the pass-through hole.

(1) Briefly, the present invention relates to a cell transplantation device provided with a plate-type carrier which has at least one pass-through hole formed on its side surface, a linear member to be threaded through the pass-through hole, and a pusher member that engages with the linear member that comes out from each exit of the pass-through hole.

(2) Moreover, a means is adopted that the pusher member is provided with arms which directly engage with the linear member and a pusher member body which supports the arms, the arms having a length so as to form a predetermined space between the carrier and the pusher member body when the arms are engaged with the linear member.

(3) Further, a means is adopted that the predetermined space is greater in height than the cells for transplantation to be mounted on the carrier.

(4) Further, the end of the arm may be, for example, V-shaped, or may have a hole through which the linear member can pass.

(5) Further, the pusher member may be provided with a stopper that makes contact with the surface in close proximity to a cell-deficient site when cells for transplantation are inserted into the cell-deficient site at the optimum position.

(6) Further, there may be two pass-through holes formed in the carrier, for example, but the number of holes is not particularly limited. In addition, the positions of the pass-through holes formed may differ in the level of the thickness of the carrier so that the pass-through holes do not cross with each other.

(7) Further, a means may also be adopted that the carrier is disk-shaped and the pass-through holes run through the center of the carrier.

(8) Further, each exit of the pass-through holes may be distributed at intervals of 90° circumferentially in the carrier.

(9) Furthermore, it is preferable for the carrier to be formed from a biodegradable material or bioabsorbable material (for example, calcium triphosphate).

BRIEF DESCRIPTION OF THE DRAWINGS

FIG. 1(A) shows a top view, while 1(B) shows a front view.

FIG. 2(A) is a front view showing the carrier before the linear members are threaded through the pass-through holes. FIG. 2(B) is a front view showing the carrier with the linear members threaded through the pass-through holes.

FIG. 11(A) is a top view and FIG. 11(B) is a front view.

FIG. 12(A) is a top view and FIG. 12(B) is a front view.

FIG. 13(A) is a top view and FIG. 13(B) is a front view.

DETAILED DESCRIPTION OF THE INVENTION

Hereinbelow, the present invention will be described in detail. The scope of the present invention is not limited by these descriptions. The present invention may be practiced, other than those illustrated below, with appropriate changes without departure from the gist of the present invention.

All the publications cited herein, for example, prior art documents, unexamined patent publications, patent applications and other references, are incorporated herein by reference.

Next, an embodiment of the present invention will be explained with reference to the drawings.

Figure 3:
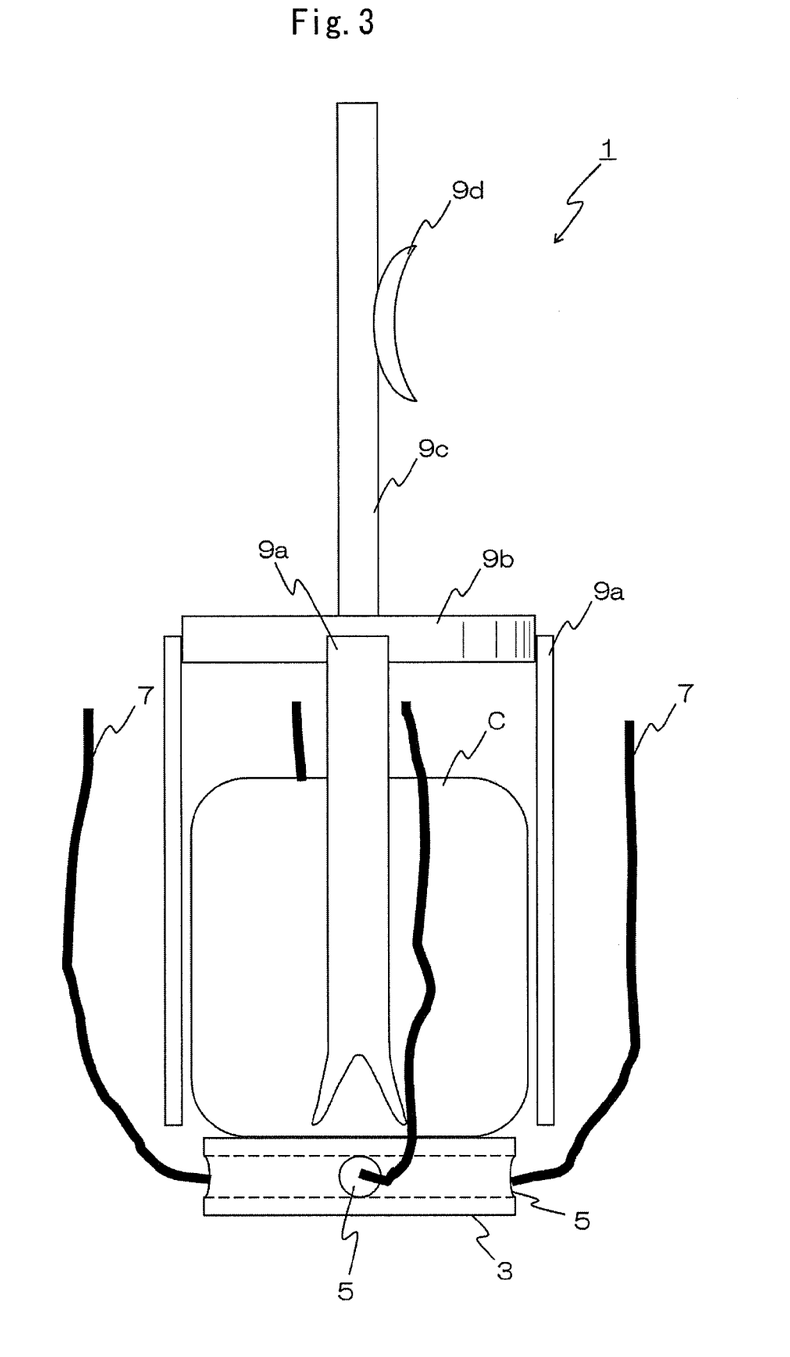
FIG. 3 is a front view showing the pusher member placed in close proximity to the carrier disclosed in FIG. 2(B).

As shown in FIG. 3, the cell transplantation device 1 pertaining to the present embodiment is composed of a plate-type carrier 3 which carries cell C (for example, cell plug) for use in transplantation; linear members 7 which are threaded through pass-through holes 5 that are formed on the side surface of carrier 3; and a pusher member 9 which engages with linear members 7 in the proximity of the exits of pass-through holes 5.

Carrier

Figure 1:
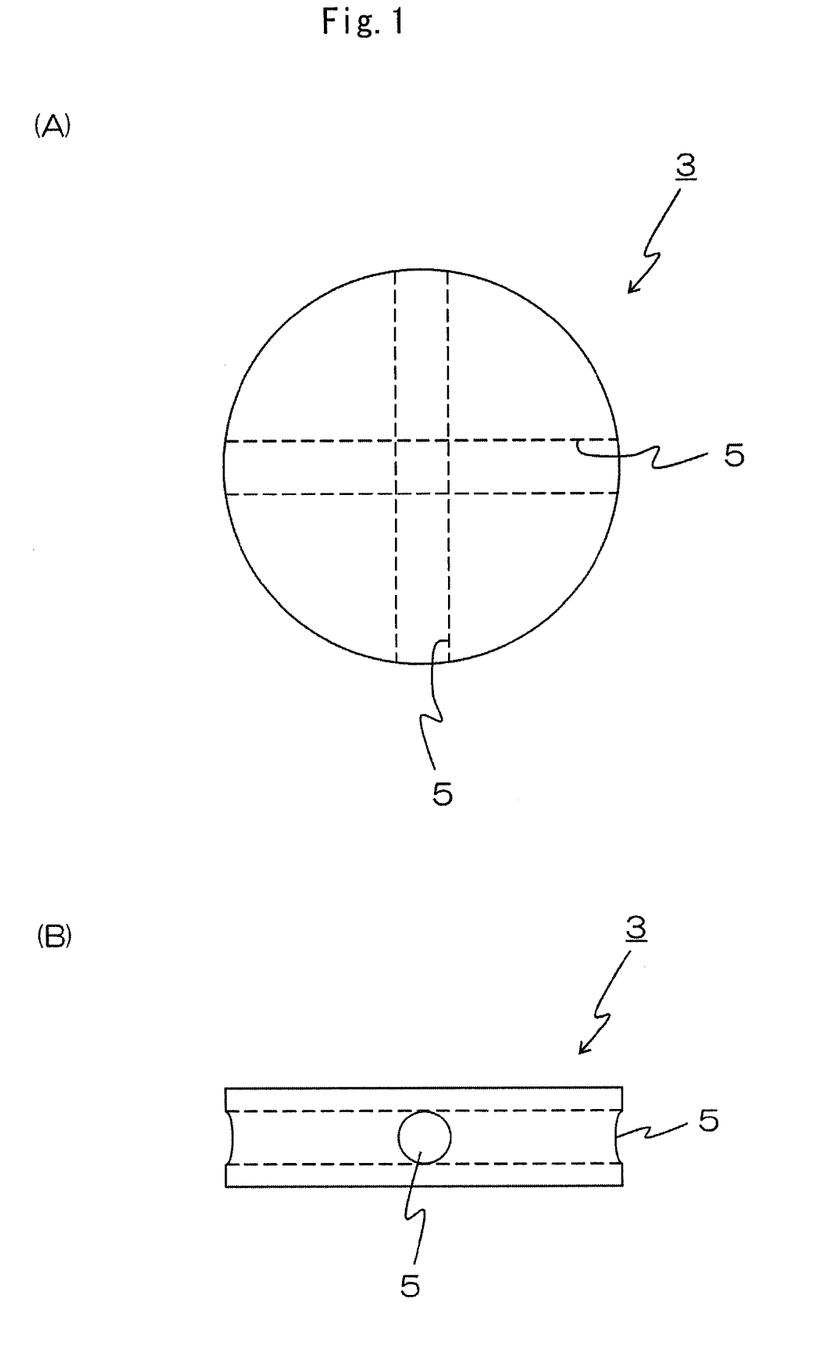
FIG. 1 is a diagram showing the carrier of the cell transplantation device pertaining to one embodiment of the present invention.

First, carrier 3 will be explained. As shown in FIG. 1, in the present embodiment, carrier 3 is disk-shaped and made of a biocompatible material, biodegradable materials, or bioabsorbable material. Carrier 3 has a flat surface and is to carry cell C for transplantation. Two pass-through holes 5 are formed on the side surface of carrier 3, making four exits on the side surface as a result. The pass-through holes 5 are for threading through linear members 7 which will be explained later.

The shape of carrier 3 is not limited to a disk and may also be a rectangular-shaped plate or other polygonal plate. Further, although calcium triphosphate is used as a material so that it will be degraded in the body after the operational procedures, other materials or substances that will be degraded or absorbed in the body may also be used in the present invention. Alternatively, even those materials that do not degrade may be used, if necessary. Other biocompatible materials, biodegradable materials, or bioabsorbable materials may be selected by one skilled in the art at one's discretion.

In the present embodiment, two pass-through holes 5 are formed so that they run through the central part (in close proximity to the center of the circle) of the carrier and make a right angle with each other. Also, in the present embodiment, since the two pass-through holes 5 are formed at almost the middle level of thickness of the carrier, they cross with other in close proximity to the center of carrier 3. The number of pass-through holes 5 is not limited to 2 and may be 1 or 3 or more. Moreover, the pass-through holes 5 do not necessarily have to run through the center of carrier 3, but may also pass through at an off-center location.

Linear Members

Figure 2:
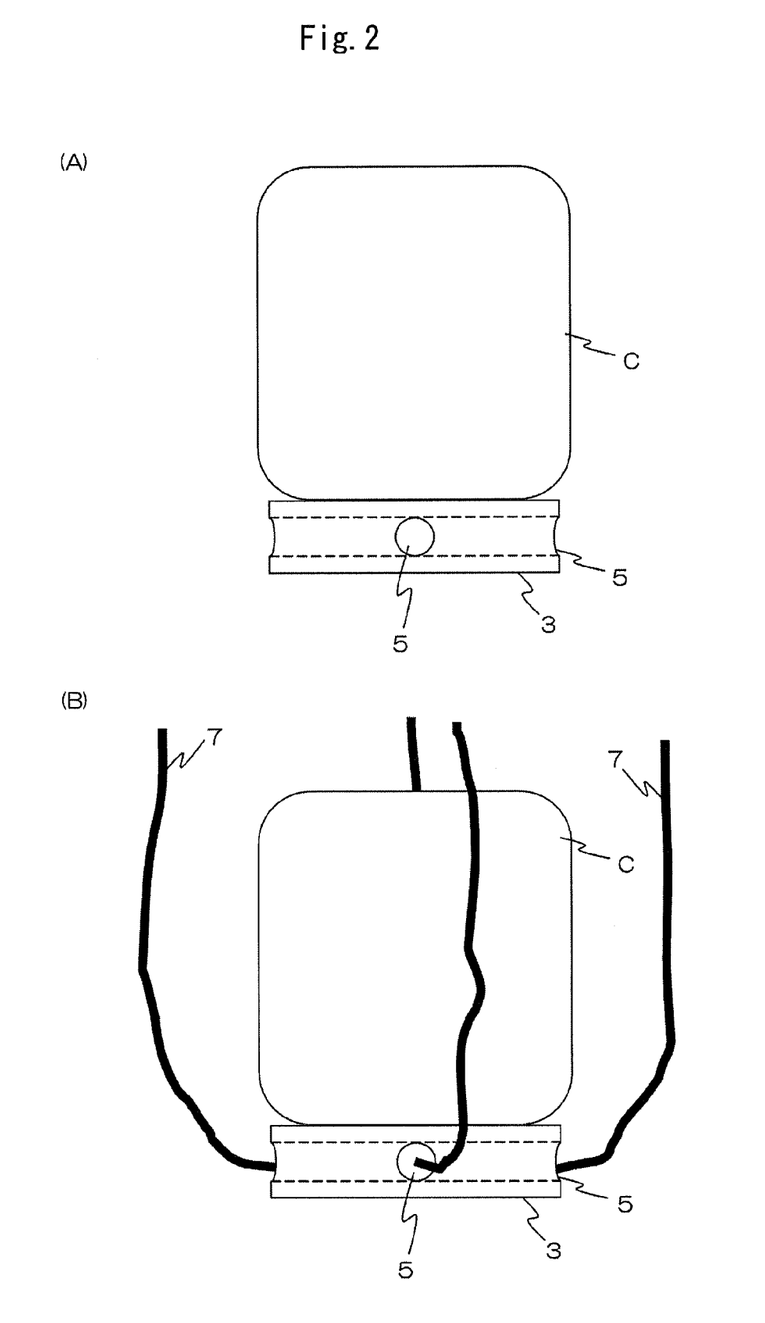
FIG. 2 is a front view showing the carrier disclosed in FIG. 1 upon which cells are mounted.

Subsequently, linear member 7 will be explained. As shown in FIG. 2, linear members 7 are threaded into pass-through holes 5 in carrier 3 and are used to support carrier 3. Although a variety of materials can be considered for use as linear member 7, nylon fiber is used in the present embodiment. This material is not limited to nylon and may also be a string made from metal wire or natural fibers. Further, the thickness of linear member 7 need only be enough to fit through pass-through holes 5 and may be thinner. Although linear members 7 are only partially shown in FIG. 2, they actually continue along in an upward direction.

Pusher Member

Subsequently, pusher member 9 will be explained. Pusher member 9 is a member that moves in cooperation with carrier 3 and linear members 7 to push cell C, which is mounted on carrier 3, into a cell-deficient site (transplantation site). As shown in FIG. 3, pusher member 9 is provided with arms 9a which engage with linear members 7, pusher member body 9b which supports arms 9a, and rod-shaped member 9c which is joined with pusher member body 9b. The end of arm 9a (lower end in the Figure) is bifurcated in a shape so as to grip linear member 7, for example in a V-shape.

Pusher member body 9b in the present embodiment is a disk-shaped material to which arms 9a are joined at the circumference. In the present embodiment, the pusher member is equipped with four arms 9a, which are located at intervals of 90° circumferentially in pusher member body 9b. In addition, since the diameter of pusher member body 9b is slightly larger than the outer diameter of cell C, even when pusher member 9 is brought into close proximity with cell C, arms 9a of pusher member 9 do not make contact with the outer wall of cell C or, in the event of contact, the form of cell C does not change or suffer damage due to the external force of arms 9a. Since arms 9a are inserted between cell C and the inner wall of a cell-deficient site when inserting cell C into the cell-deficient site, it is preferable for arms 9a to be as thin as possible.

Further, linear member coiling means 9d for coiling and thereby securing the linear member 7 may also be affixed to rod-shaped member 9c of pusher member 9. This linear member coiling means 9d protrudes from the surface of rod-shaped member 9c in an approximate V-shape, and linear member 7 can be prevented from tangling by coiling thread member 7 in the gap between rod-shaped member 9c and linear member coiling means 9d. However, this linear member coiling means 9d is not essential for the present invention.

Cells

The cells used in the invention are undifferentiated cells such as stem cells (ES cells, umbilical cord blood-derived cells, undifferentiated mesenchymal stem cells, etc.) and the differentiated cells thereof. Since the differentiation of osteoblast cells, chondrocytes, and fat cells can be easily induced from undifferentiated mesenchymal stem cells, these differentiation-induced cells (articular chondrocytes, osteocytes) may also be used. Moreover, adult mesenchymal stem cells may also be used.

It is preferable that cell C mounted on carrier 3 is three-dimensional. Known methods may be utilized in order to construct a three-dimensional cell C (See, for example, Unexamined Patent Publication No. 2004-357694). Briefly, a cultivation chamber in which cells are put is shaped into a desired shape. Then, cells in aggregation (spheroids) are cultured in the chamber. As a result, a cell construct that has been constructed three-dimensionally into a desired shape corresponding to the chamber's shape is obtained.

Function

Figure 4:
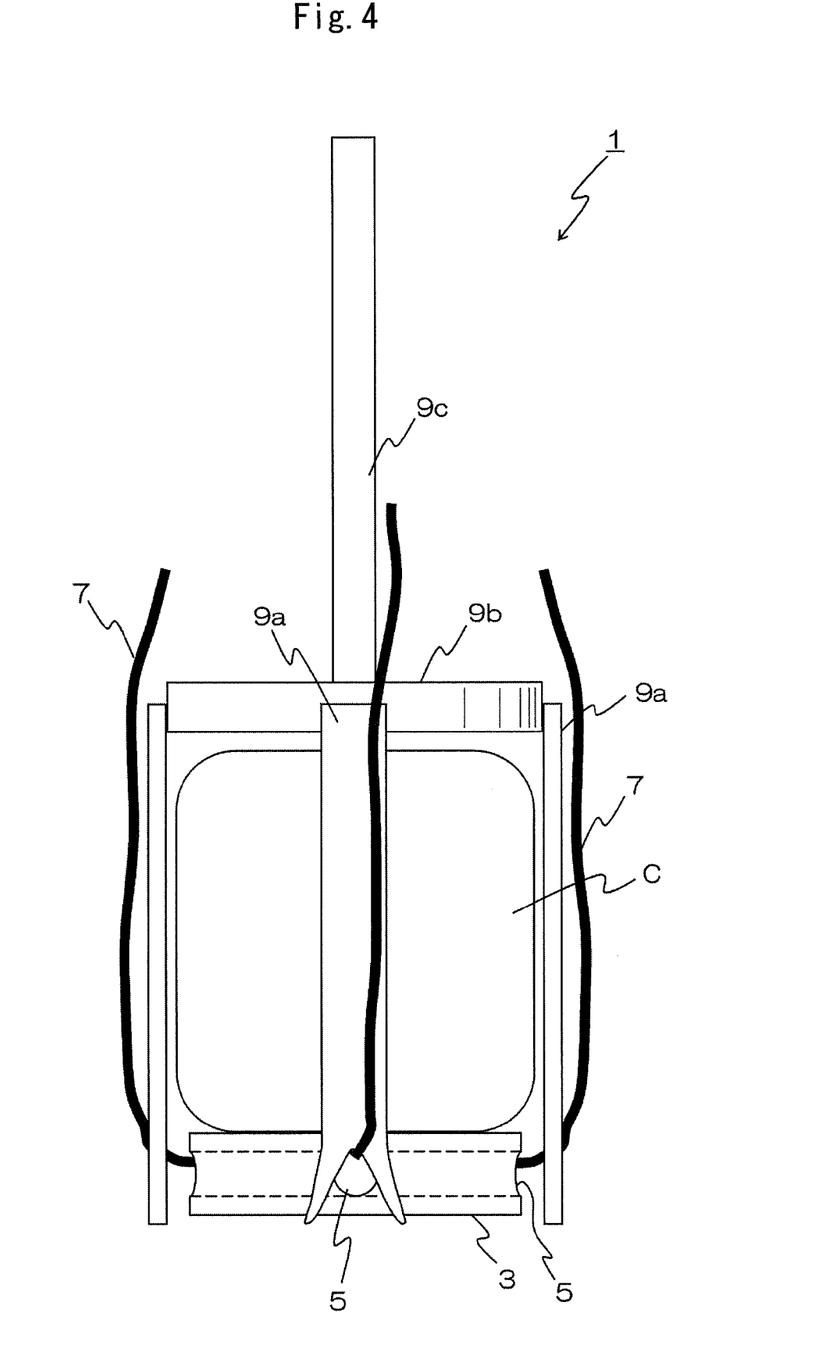
FIG. 4 is a front view showing the linear members engaged with the arms of the pusher member.

The following is an explanation of the functions of the cell transplantation device pertaining to the present embodiment. First, as shown in FIG. 2(A), the desired cell C for transplantation is mounted on the surface of carrier 3. Next, as shown in FIG. 2(B), two linear members 7 are passed through the two pass-through holes 5 formed on the side surface of carrier 3. Then, the four ends of the linear members 7 are gripped and lifted equally. In this way, carrier 3 is lifted up while remaining almost level. In this state, as shown in FIG. 3, pusher member 9 is moved closer to linear members 7 which are coming out from the four exits of the pass-through holes 5, and positioned so that the end of the V-shaped arm 9a grips each linear member 7. Subsequently, pusher member 9 is moved a little further down so that arms 9a engage with linear members 7. As a result, a specific amount of tension will be produced in linear members 7, and, as shown in FIG. 4, cell C will be securely retained through carrier 3 due to cooperation of pusher member 9 and linear members 7. At this point, the length of arm 9a is such that pusher member body 9b does not contact the surface of cell C, or, if contact is made, the shape of cell C is not altered. Accordingly, absolutely no unnecessary external force is exerted on cell C, and cell C is not damaged.

Figure 5:
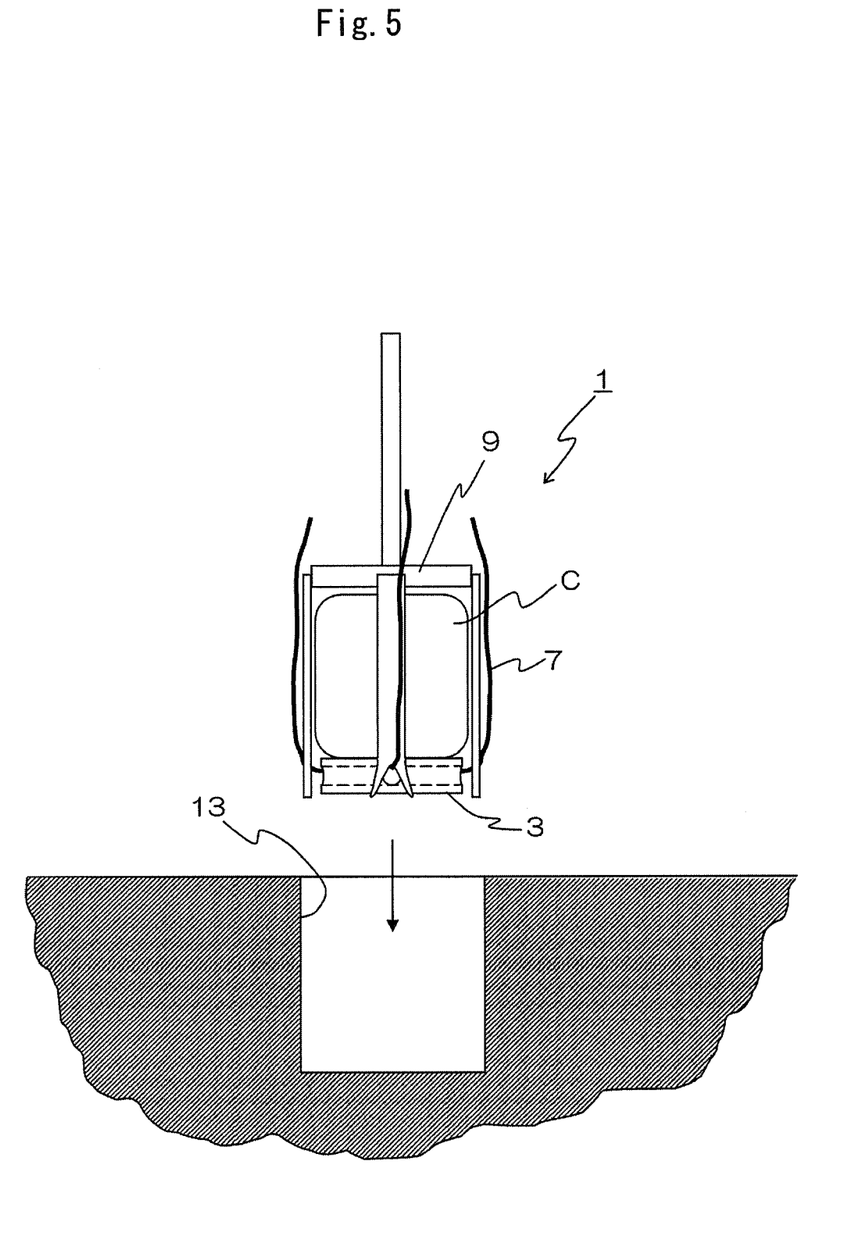
FIG. 5 is a partial cross-section showing the cell transplantation device disclosed in FIG. 4 placed in close proximity to a cell-deficient site.
Figure 6:
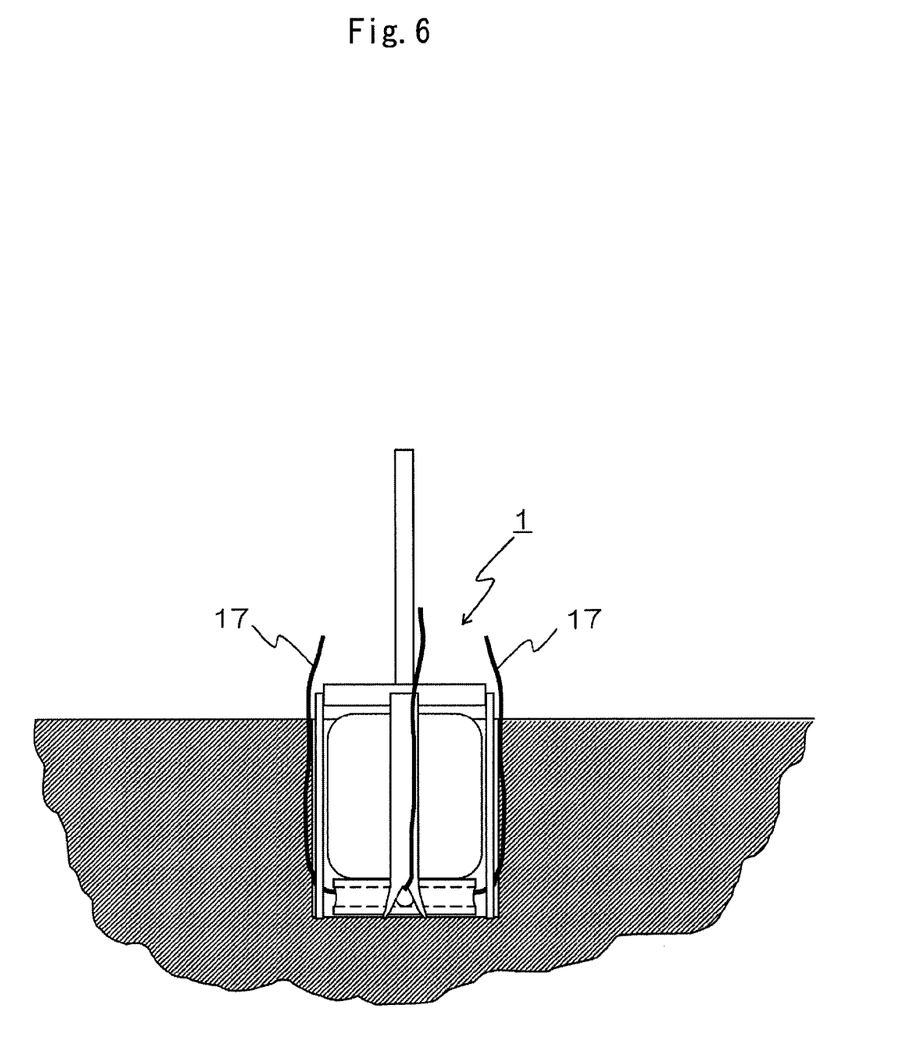
FIG. 6 is a partial cross-section showing the cell transplantation device and cells inserted into the cell-deficient site.

Next, as shown in FIG. 5, cell C which is retained by means of pusher member 9 and linear members 7 is inserted into cell-deficient site 13. Specifically, a hole slightly larger than cell C in diameter is formed in advance in cell-deficient site 13. Then, cell C is inserted together with linear members 7 and pusher member 9. Since cell C is securely supported by linear members 7 and pusher member 9 through carrier 3 at this point in time, cell C can be positioned easily at the optimum depth of cell-deficient site 13 by operating pusher member 9 as seen in FIG. 6. Specifically, it is preferable for the surface of cell C to be approximately 1 mm raised in comparison to the area surrounding cell-deficient site 13. In this way, cell regeneration at cell-deficient site 13 results in a smooth surface. Particularly in the present embodiment, cell C can be pulled out by means of linear members 7 even if cell C has been mistakenly driven too far into the cell-deficient site.

Figure 7:
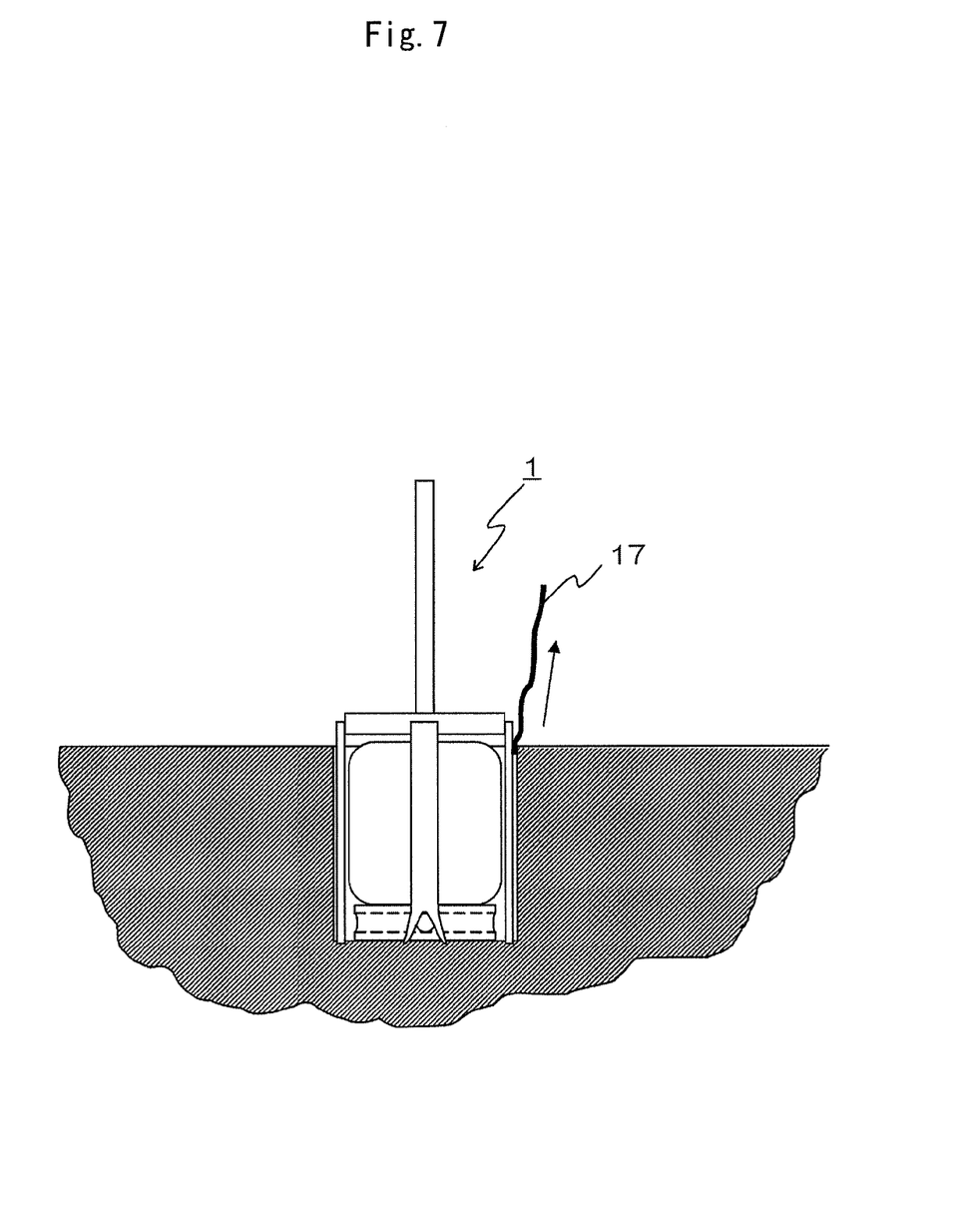
FIG. 7 is a partial cross-section showing the linear member withdrawn from the pass-through hole of the carrier.
Figure 8:
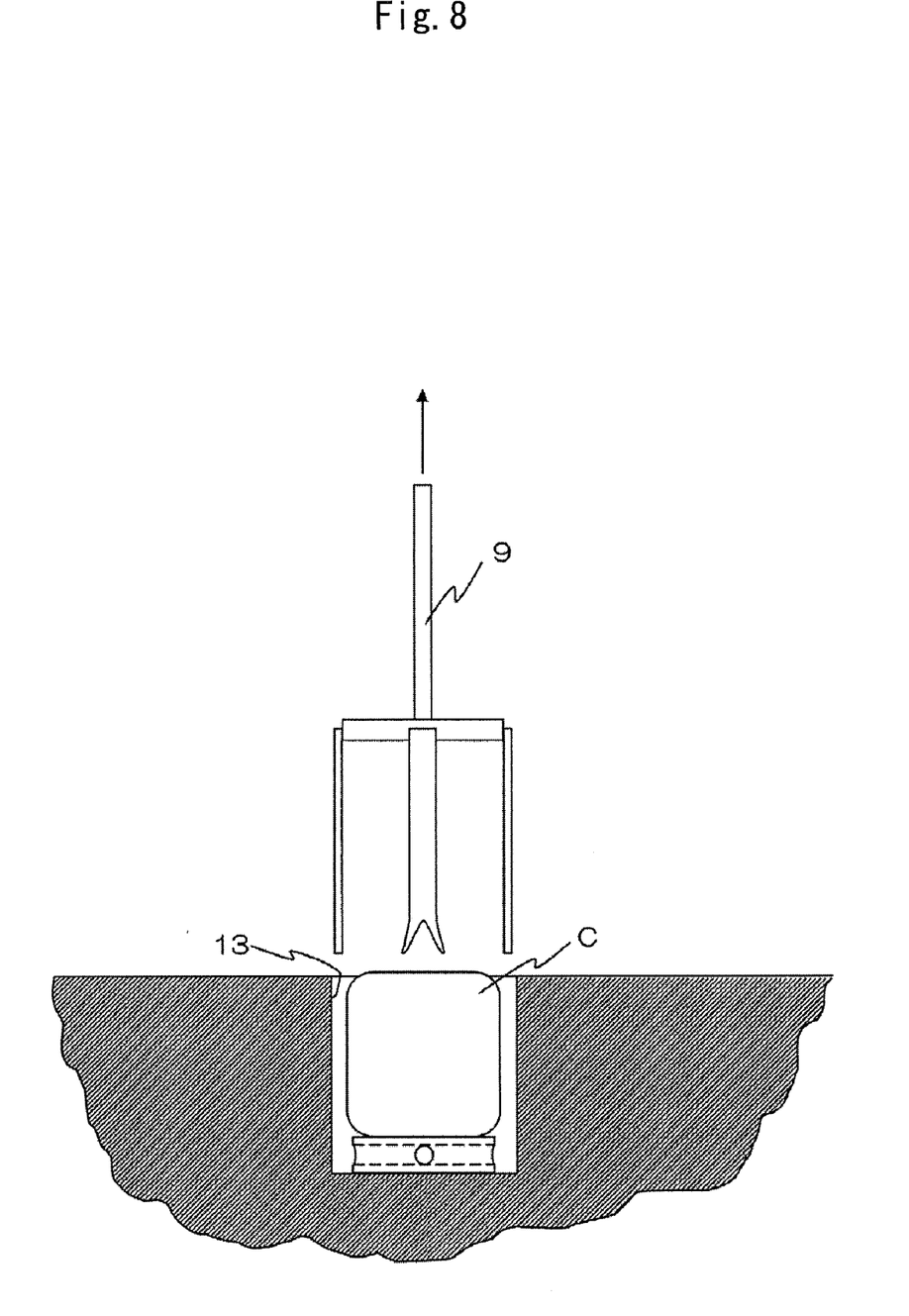
FIG. 8 is a partial cross-section showing the pusher member withdrawn from the pass-through holes of the carrier.

Once optimum positioning of cell C has been achieved, linear members 7 are removed from pass-through holes 5 of member 3 as shown in FIG. 7. Specifically, linear members 7 can be easily pulled out by pulling one end of each linear member 7. At this point in time, if an attempt is made to pull linear member 7 quickly, carrier 3 will be pulled out simultaneously; so linear member 7 should be pulled out slowly. Next, pusher member 9 is pulled out as shown in FIG. 8. Through a series of these operations, cell C is optimally positioned on the cell-deficient site. Although a gap is shown between cell C and the inner wall of the cell-deficient site in FIG. 8, this gap is for the sake of explanation. In reality, cell C is inserted into the cell-deficient site in such a manner that there is almost no gap.

Figure 9:
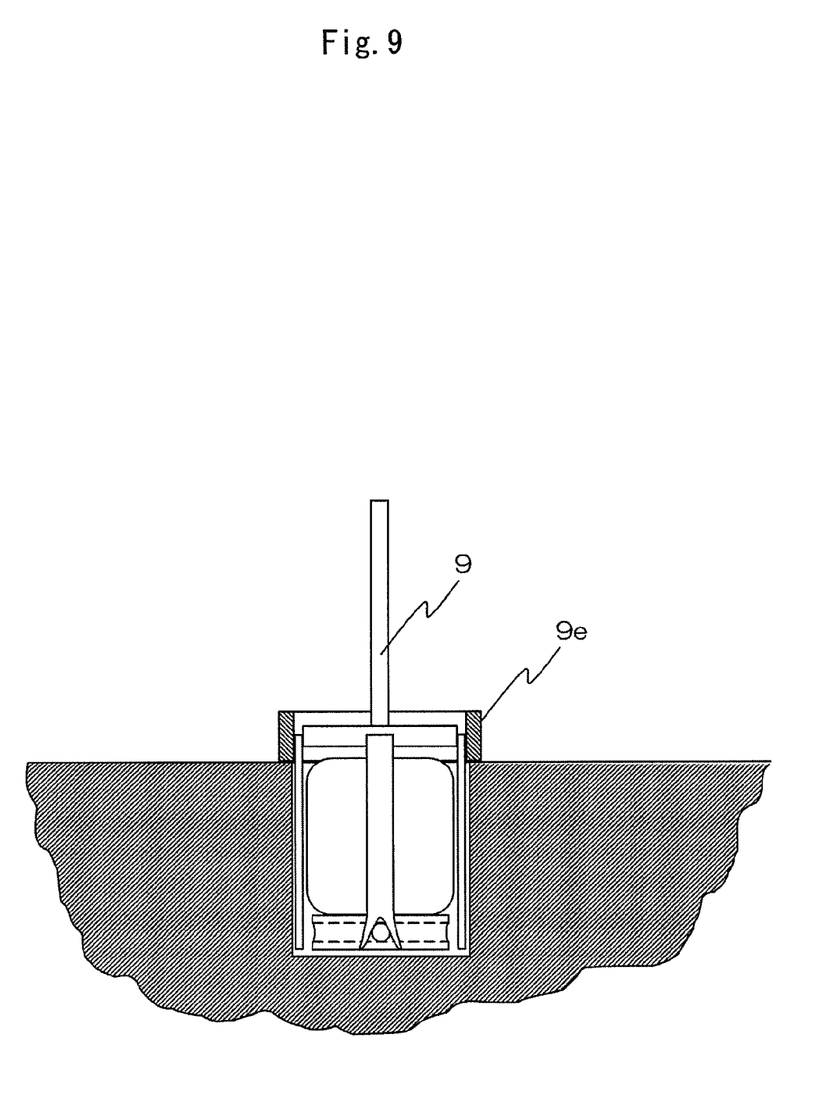
FIG. 9 is a partial cross-section showing the cell transplantation device pertaining to the 2nd embodiment of the present invention.

Subsequently, another embodiment of the present invention will be described. As shown in FIG. 9, this embodiment is different from the above embodiment in terms of the pusher structure. The other parts are identical to those in the above embodiment. The pusher member 9 of this embodiment is characterized by being equipped with a stopper 9e that contacts the surface surrounding the cell-deficient site. This stopper 9e is a tube-shaped part fixed so that it covers the upper tip of arm 9a. The position of stopper 9e is set so that cell C will be positioned properly when the bottom edge of stopper 9e makes contact with the surface around the cell-deficient site.

By installing stopper 9e on the outside of arm 9e in this way, the inconvenience of cells being pushed down too far is prevented. As a result, the technician can transplant cell C free from concerns about depth. It should be noted that the structure of stopper 9e is just an example; stopper structure is not limited to this. In other words, not a tube-shaped member but a plurality of arm-shaped members may be used. Alternatively, a protrusion may be provided at the end of the arms.

Figure 10:
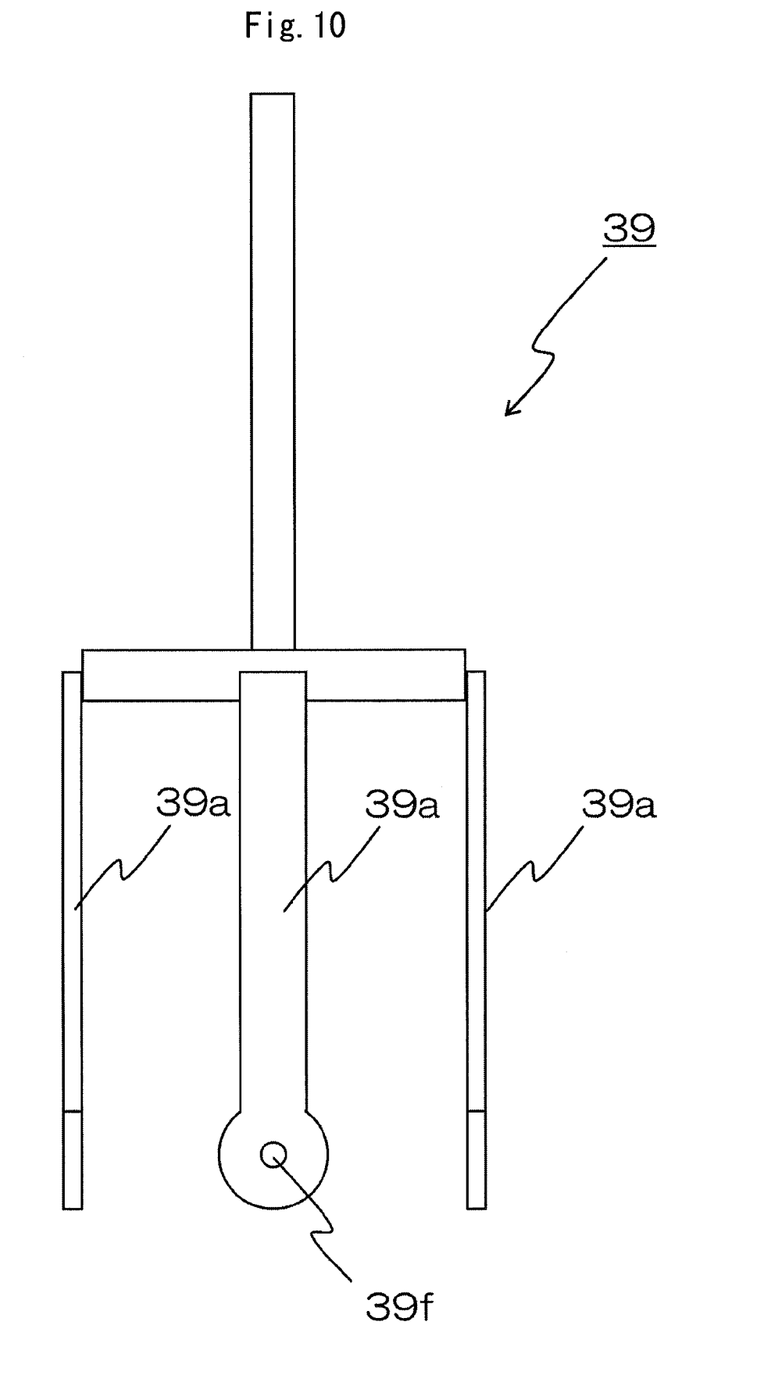
FIG. 10 is a front view showing the pusher member of the cell transplantation device pertaining to the $3^{rd}$ embodiment of the present invention.

Subsequently, a further embodiment will be described (FIG. 10). This embodiment is also characterized by the structure of the pusher member, and the other parts are identical to those in the above embodiment. In pusher member 39 of this embodiment, arm 39a has a round, not V-shaped, end with a hole 39f formed at the center of the end. By forming a hole 39f on the tip of arm 39a and threading a linear member through this hole 39f, the linear member does not miss arm 39a, even when the tension of the linear member becomes low.

Figure 11:
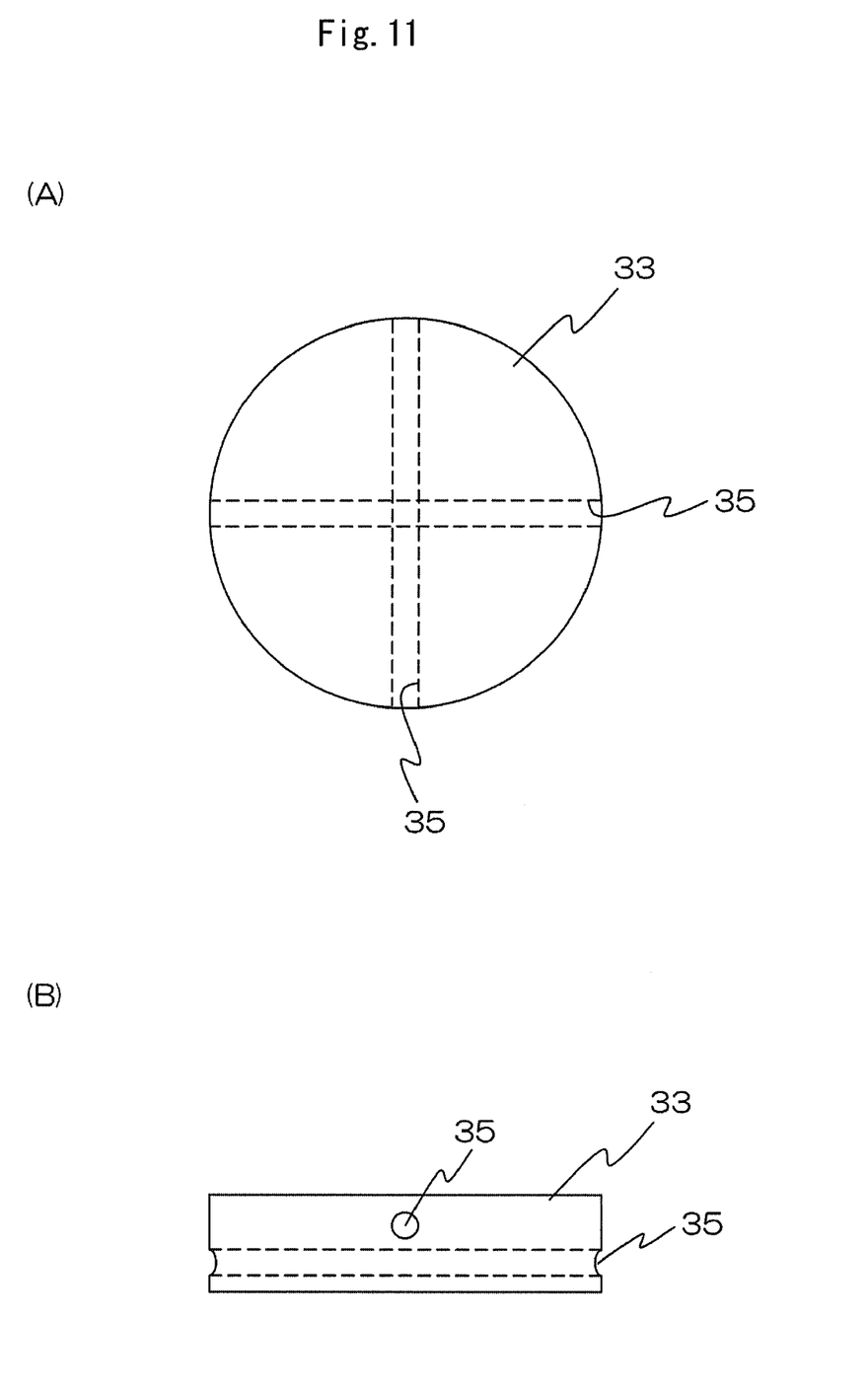
FIG. 11 shows the carrier of the cell transplantation device pertaining to the 4$^{th}$ embodiment of the present invention where

Subsequently, an embodiment of the present invention will be described (FIG. 11). This embodiment is different from the above embodiments in terms of the carrier structure, but the other parts are identical to those of the other embodiments. Carrier 33 of this embodiment is characterized by the positional relationship of its two through-holes 35. Specifically, as shown in FIG. 11, these through-holes 35 are formed at different levels of the thickness of carrier 33. This is designed so that the pass-through holes 35 do not cross directly with each other at the center of carrier 33. This design is employed so that, when the two linear members run through pass-through holes 35 making a right angle with another, one linear member does not impede the pass-through of the other. In other words, when each pass-through hole 35 is independent, two linear members will easily pass through the holes 35 without encountering each other.

Figure 12:
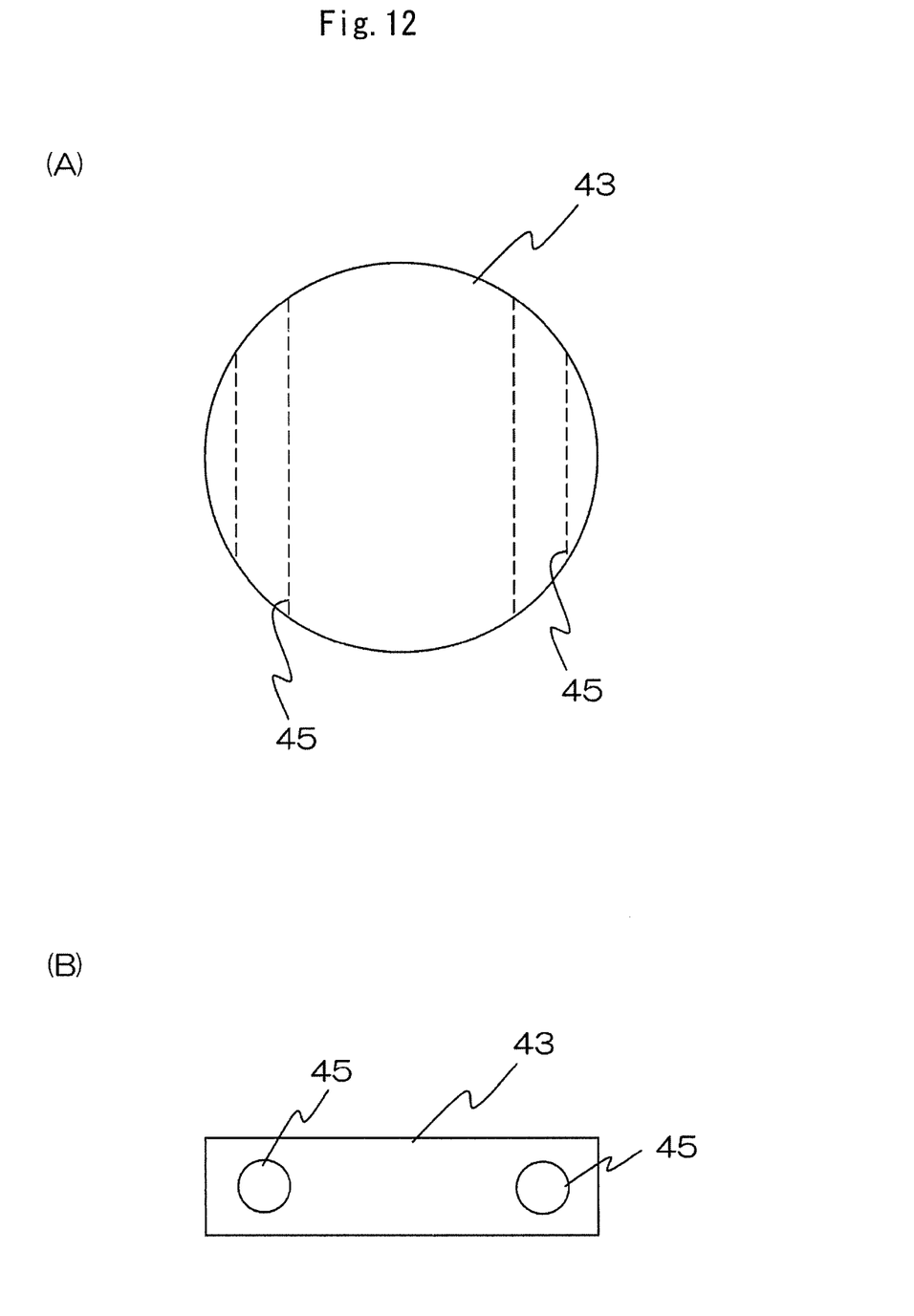
FIG. 12 shows the carrier of the cell transplantation device pertaining to the 5$^{th}$ embodiment of the present invention where

Subsequently, another embodiment will be described (FIG. 12). The carrier structure in this embodiment differs from that in the above embodiment, but the other parts are identical to those in the above embodiment. Carrier 43 in this embodiment is also characterized by the positional relationship of its two pass-through holes 45. Specifically, as shown in FIG. 12, each pass-through hole 45 does not run through the center of the carrier 43, but is positioned so that it forms a chord in relation to the outer circumference of carrier 43. In this embodiment especially, two pass-through holes 45 are formed parallel to each other. By adopting this constitution, as explained in the section on the above embodiment, two linear members can pass easily through pass-through holes 45 without encountering each other.

Figure 13:
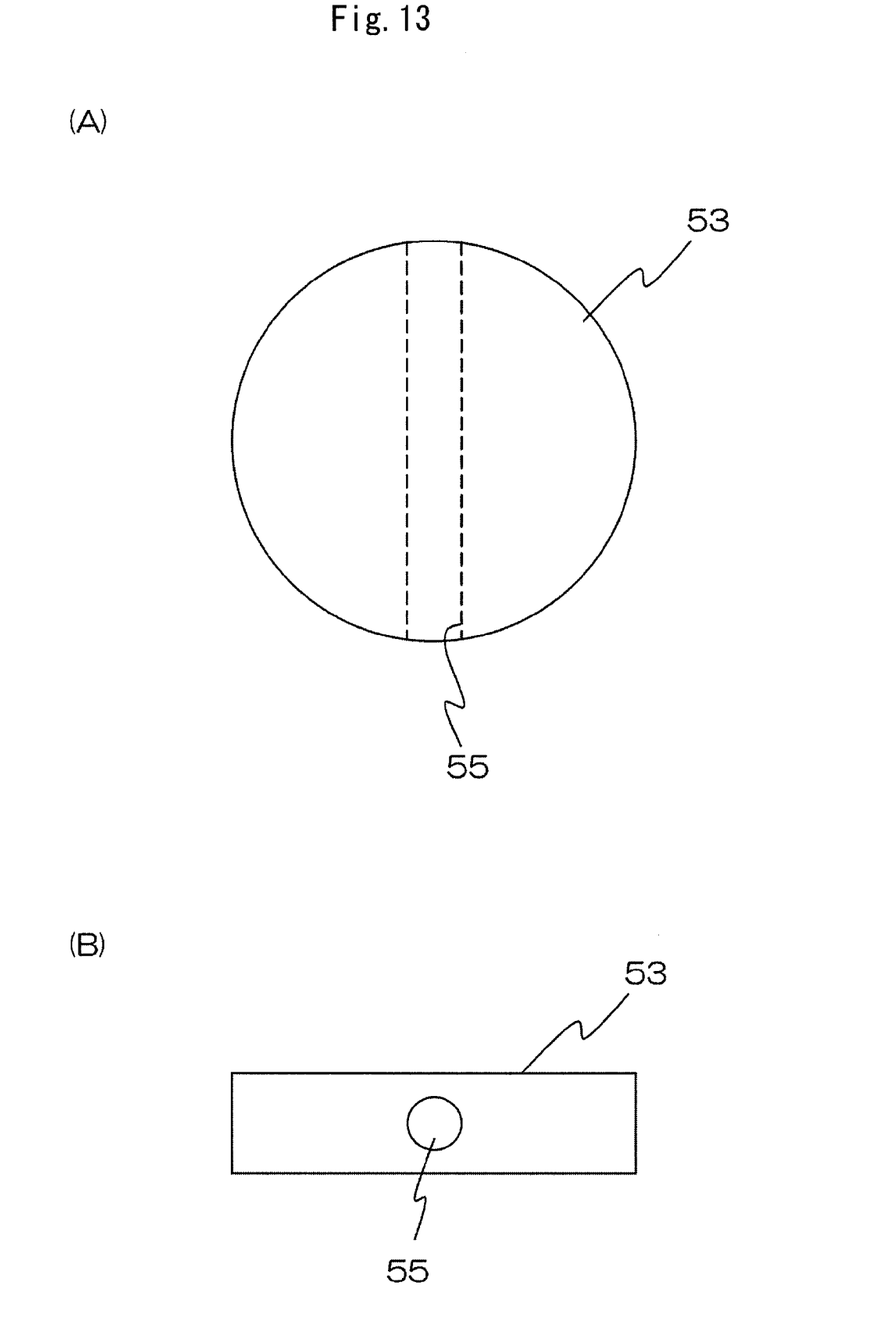
FIG. 13 shows the carrier of the cell transplantation device pertaining to the 6$^{th}$ embodiment of the present invention where

Subsequently, a further embodiment will be described (FIG. 13). This embodiment is different from embodiment in terms of the carrier structure, but the other parts are identical to those of the above embodiments. The carrier 53 of this embodiment is characterized by having a single through hole 55. Specifically, as shown in FIG. 13, a pass-through hole 55 is formed through the center of carrier 53, and one linear member is to be threaded through this pass-through hole 55. By reducing the number of pass-through holes to one in this way, the cost of manufacturing the carrier 53 can be cut. However, when there is only a single pass-through hole 55, some measures must be taken so that the cell does not fall over along with carrier 53. In order to prevent this, it is necessary to provide arms of the pusher member even at locations away from the pass-through holes.

In the present invention, cells for transplantation are mounted upon a carrier provided with pass-through holes through which linear members are threaded. Then, the linear members are engaged with a pusher member. By using such a device, it is possible to easily determine the position of the cells for transplantation at a cell deficient site without applying direct external force to the cells.

The present invention is applicable to devices for cell transplantation.

The invention claimed is:

1. A cell transplantation device comprising:
a plate-type carrier which has at least one pass-through hole formed on its side surface,
a linear member to be threaded through the pass-through hole, and
a pusher member which engages with the linear member when the linear member comes out from each exit of the pass-through hole; wherein the pusher member comprises arms that directly engage with the linear member and a pusher member body that supports the arms, said arms having a length so as to form a predetermined space between the carrier and the pusher member body when the arms are engaged with the linear member.

2. The cell transplantation device according to claim 1, wherein the predetermined space is greater in height than a cell for transplantation to be mounted on the carrier.

3. The cell transplantation device according to claim 1, wherein the end of the arm is V-shaped.

4. The cell transplantation device according to claim 1, wherein the end of the arm has a hole through which the linear member can pass.

5. The cell transplantation device according to claim 1, wherein the pusher member comprises a stopper that makes contact with a surface around a cell-deficient site when a cell for transplantation is inserted into the cell-deficient site at the optimum position.

6. The cell transplantation device according to claim 1, wherein the carrier has two pass-through holes formed therein.

7. The cell transplantation device according to claim 6, wherein positions of the pass-through holes formed differ in the level of the thickness of the carrier so that they do not cross with each other.

8. The cell transplantation device according to claim 1, wherein the carrier is disk-shaped and the pass-through holes run through the center of said carrier.

9. The cell transplantation device according to claim 6, wherein each exit of the pass-through holes is distributed at intervals of 90° circumferentially in the carrier.

10. The cell transplantation device according to any claim 1, wherein the carrier is made of a biodegradable material or bioabsorbable material.

* * * * *

UNITED STATES PATENT AND TRADEMARK OFFICE
CERTIFICATE OF CORRECTION

| | |
|---|---|
| PATENT NO. | : 8,246,570 B2 |
| APPLICATION NO. | : 12/809104 |
| DATED | : August 21, 2012 |
| INVENTOR(S) | : Yukihide Iwamoto et al. |

It is certified that error appears in the above-identified patent and that said Letters Patent is hereby corrected as shown below:

Title Page (73) Assignees should read:   Kyocera Medical Corporation, Osaka (JP)
　　　　　　　　　　　　　　　Yukihide Iwamoto, Fukuoka (JP)
　　　　　　　　　　　　　　　Koichi Nakayama, Fukuoka (JP)

Signed and Sealed this
Eighth Day of January, 2013

David J. Kappos
*Director of the United States Patent and Trademark Office*